(12) United States Patent
McKinley

(10) Patent No.: US 6,837,444 B1
(45) Date of Patent: Jan. 4, 2005

(54) FLUID FILTRATION DEVICE

(76) Inventor: Kevin L. McKinley, 1616 Santa Clara St., Richmond, CA (US) 94804

( * ) Notice: Subject to any disclaimer, the term of this patent is extended or adjusted under 35 U.S.C. 154(b) by 340 days.

(21) Appl. No.: 10/053,176

(22) Filed: Jan. 18, 2002

Related U.S. Application Data

(60) Provisional application No. 60/262,296, filed on Jan. 19, 2001.

(51) Int. Cl.[7] ................................................ A24F 25/00
(52) U.S. Cl. .............................. 239/34; 239/55; 239/56
(58) Field of Search ....................................... 239/34–60

(56) References Cited

U.S. PATENT DOCUMENTS 3,702,677 A * 11/1972 Heffington .................. 239/55
4,058,425 A * 11/1977 Thrun ........................ 156/200
4,161,284 A * 7/1979 Rattan ......................... 239/43
4,345,716 A * 8/1982 Armstrong et al. ........... 239/56
5,133,458 A * 7/1992 Miller ........................ 206/530
6,039,488 A * 3/2000 Krawczyk et al. .......... 401/132

* cited by examiner

*Primary Examiner*—Dinh Q. Nguyen
(74) *Attorney, Agent, or Firm*—Theodore J. Bielen, Jr.

(57) ABSTRACT

A fluid filtration device utilizing envelope constructed of a frangible material and forming a closed interior chamber for holding a charge of volatile scented material. A flexible shield encloses the envelope and is permeable in a controlled manner to the volatile scented material once the envelope has been shattered.

5 Claims, 2 Drawing Sheets

FLUID FILTRATION DEVICE

CROSS-REFERENCES TO RELATED APPLICATION

The present application is based on Provisional Application 60/262,296, filed 19 Jan. 2001.

BACKGROUND OF THE INVENTION

The present invention relates to a novel fluid filtration device.

Fluid filters, such as filters associated with heating systems and ducting, have been formed into cartridges or packs consisting of a frame and a filtration material, normally of paper or plastic consistency. Although successful in capturing solid particles, which are finely divided, odors are still capable of passing from a fluid delivery source to an occupied space through the ducting system.

In the past, various vapor dispensers have been designed to scent the air breathed by an occupant in a vehicle or office.

For example, strips of porous material impregnated with scented material have been employed by hanging the same to walls or other structures within the compartment or space. In addition, canisters have been used to slowly deliver scented material by opening the same. However, canisters are inconvenient in placement and are unaesthetic.

A scented fluid filtration system would be a notable advance in the field of environmental controls.

BRIEF SUMMARY OF THE INVENTION

In accordance with the present invention a novel and useful fluid filtration device is herein provided.

A fluid filtration device of the present invention includes as one of its elements an envelope which is constructed of a frangible material. An envelope forms a closed interior chamber which is accessed by breaking the envelope. For example, the envelope may be made of any glass, plastic, ceramic, or other material which possesses this characteristic.

A predetermined charge of volatile scented material is placed in the envelope. The scented material is either hermetically sealed or enclosed in the envelope by a stopper or cap which is not intended to be removable. The scented material may take the form of any perfume or other aromatic or pleasantly fragrant compound. The scented material may be in the form of a fluid such as liquid or gas which tends to diffuse to the adjacent atmosphere when released from the chamber of the envelope.

A flexible shield encloses the envelope at least in part. Such flexible shield may take the form of a strip of polymeric material such as polyethylene. Such material would allow a force to be exerted on the envelope, yet prevent pieces or chards of the envelope from escaping the shield. The shield also possesses permeability to the volatile scented material and regulates release of the same.

In certain cases, the fluid filtration device may include a cartridge or plat. Such cartridge may take the form of a first partition and a second partition which sandwich the envelope therewithin. The first partition would be connected to the second partition by adhesive means or by the use of a frame formed about the perimeter of the sandwiched partitions. The first and second partitions may be constructed of flexible material to allow a force to be exerted through at least one of the partitions, the shield, and to the exterior of the envelope to break the same for releasing of the volatile scented material. The cartridge may be placed in a filtration system in a vehicle or edifice.

It may be apparent that a novel and useful fluid filtration device has been hereinabove described.

It is therefore an object of the present invention to provide a fluid filtration device which is amenable to insertion in a filter for a vehicle or edifice ventilation system.

Another object of the present invention is to provide a fluid filtration device which is capable of releasing scented material over a relatively long period of time within an existing filtration system for a vehicle or edifice.

Another object of the present invention is to provide a fluid filtration device which acts in conjunction with a filter cartridge for a ventilation system which is intended to filter solid particulate matter and to release scented material into a compartment or space.

A further object of the present invention is to provide a fluid filtration device which is simple and easy to activate and provides scented gases to a space concomitant with the filtration of solid particles therefrom in a filtration system.

A further object of the present invention is to provide a fluid filtration device which very closely controls the release of volatile scented material over a period of time in a space found in a vehicle or edifice.

Another object of the present invention is to provide a fluid filtration device which is simple and easy to employ in a standard filtration system which scents the air exiting a filtration system and also cleans particulate matter therefrom.

The invention possesses other objects and advantages especially as concerns particular characteristics and features thereof which will become apparent as the specification continues.

Figure 1:
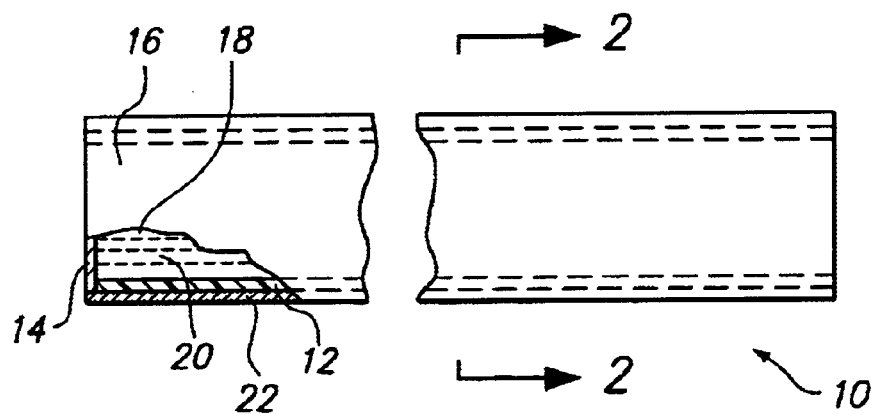
FIG. 1 is a side elevational view of the envelope portion of the present invention with a broken away part depicted in elevation.

For a better understanding of the invention reference is made to the following detailed description of the preferred embodiments thereof which should be taken in conjunction with the hereinabove described drawings.

DETAILED DESCRIPTION OF THE PREFERRED EMBODIMENTS OF THE INVENTION

Various aspects of the present invention will evolve from the following detailed description of the preferred embodiments thereof which should be completely understood only by comparing the same to the prior described drawings.

The preferred embodiment of the invention as a whole is shown in the drawings by reference character 10. Fluid filtration device 10 includes as one of its elements an envelope 12 which is constructed of any suitable frangible material. For example, envelope 12 may be formed to a tube of glass which is sealed at both ends through manufacturing techniques or by use of stoppers. End 14 represents the sealing of seal for end portion 16 of tube 12, in this regard. Frangible envelope 12 may be formed of any other suitable material such as plastic, ceramic matter, and the like. In any case, envelope 12 is intended to break in whole or in part upon the application of an exterior force to envelope 12. Envelope 12 also forms a chamber 18, therewithin, which is closed to the external environment.

A predetermined charge or quantity of volatile scented material 20 is found within chamber 18 of envelope 12. It should be realized that scented material is charged into chamber 18 prior to sealing of the same.

A flexible shield 22 at least partially surrounds envelope 12. Flexible shield 22 may be formed of any suitable material such as a polymeric sheet, such as one constructed of polyethylene. Shield 22 permits the application of a force to envelope 12 in order to shatter or break the same to release volatile scented material 18 therefrom. In addition, shield 22 prevents shards or pieces of envelope 20 from escaping and serves to control the rate of diffusion of scented volatile material from chamber 18 over a period of time. For example, scented material may escape from envelope 12 over a matter of months when envelope 12 is used in a ventilation system, which will be more fully discussed hereinafter.

Figure 2:
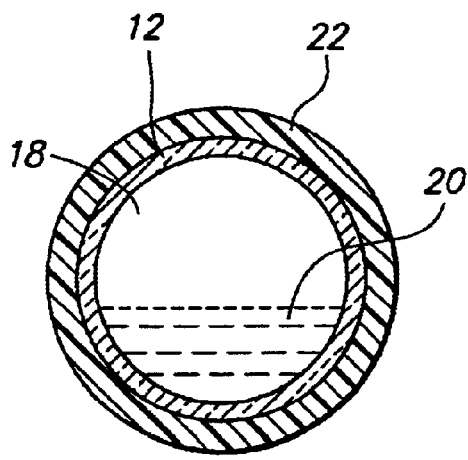
FIG. 2 is a sectional view taken along line 2—2 of FIG. 1.
Figure 3:
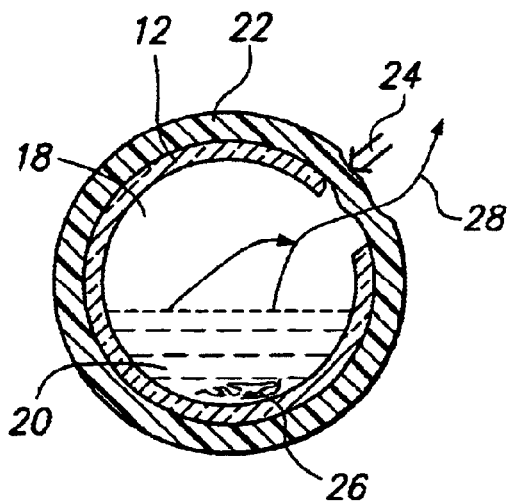
FIG. 3 is a further rendition of FIG. 2 indicating the breaking of the envelope to release volatile scented material therefrom.

FIGS. 1–3 represent device 10 in its basic format. FIG. 3 in particular shows the application of a force, directional arrow 24, which has created plurality of shards 26 within chamber 18 of envelope 12, FIG. 3. Directional arrows 28 indicate the release of scented vapor from chamber 18 and through shield 22 at a controlled rate. It should be noted that scented material 20 may be in the form of gas or liquid within chamber 18 initially. Of course, gaseous scented material passes through shield 22 when envelope 12 has been broken.

Figure 4:
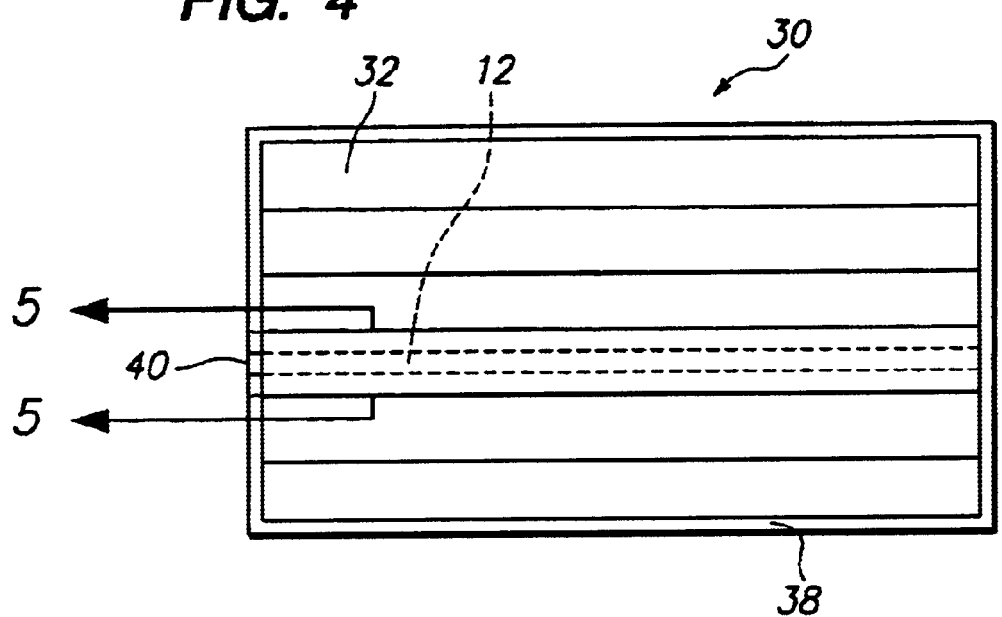
FIG. 4 is a top plan view of a filter cartridge incorporating the envelope of FIG. 1 therewithin.
Figure 5:
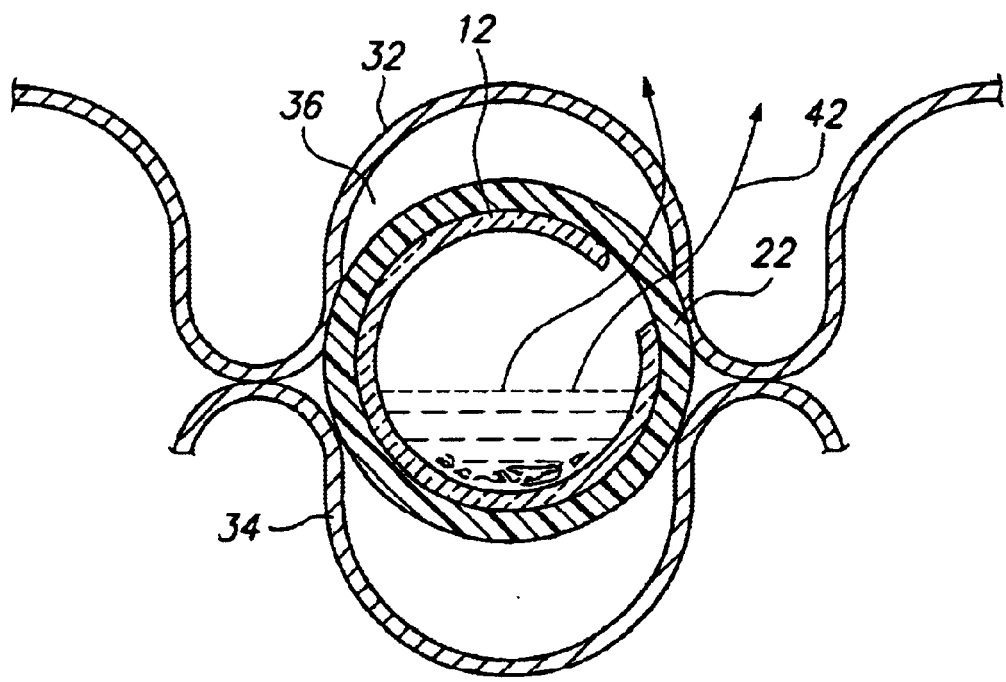
FIG. 5 is a sectional view taken along line 5—5 of FIG. 4.

Turning to FIG. 4, it may be observed that envelope 12 may be placed within a filter cartridge 30. Filter cartridge 30 includes a first partition 32 and a second partition 34. First and second partitions 32, 34 are convoluted as depicted in FIG. 5. Central space 36 holds envelope 12 as shown. Frame 38 confines partitions 32 and 34 in a sandwich configuration. A plug 40 through frame 38 permits the insertion of device 10, specifically envelope 12 surrounded by shield 22, within cartridge 30.

In operation, the user merely applies pressure to the exterior of device 10 through shield 22 to break envelope 12. Volatile scented material 20 will pass through the broken portion of envelope 12 and shield 22 at a controlled rate. Shards 26 of envelope 12 will not pass through shield 22. In the embodiment depicted in FIGS. 4 and 5, device 10 is inserted within a filter cartridge 30 through a space 36 which is accessed via plug 40. Again, the user merely applies force to the exterior of partition 32 or 34 to break envelope 12 and permit the controlled release of scented material through shield 22, directional arrows 42, FIG. 5. It has been found that scented material will permeate the surrounding environment through a ventilation system employing filter cartridge 34 for a relatively long period of time in a safe and efficient manner.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A fluid filtration device, comprising:
   a. an envelope, said envelope being constructed of a frangible material, said envelope forming a closed interior chamber;
   b. a predetermined charge of volatile scented material, said scented material being located within said interior chamber of said envelope;
   c. a flexible shield at least partially enclosing said envelope, said flexible shield being permeable to said volatile scented material and serving as a container for divided portions of said envelope, said shield allowing transmission of a force to break said envelope therewithin;
   d. a first partition;
   e. a second partition; and
   f. means for connecting said first partition to said second partition to form a chamber, said envelope positioned within said chamber, at least said first partition being permeable to said volatile scented material.

2. The device of claim 1 in which said flexible shield comprises a layer of polymeric material.

3. The device of claim 2 in which said layer of polymeric material comprises polyethylene.

4. The device of claim 1 in which said envelope comprises an elongated tube.

5. The device of claim 4 in which said elongated tube comprises a glass tube.

* * * * *